United States Patent
Tanabe et al.

(10) Patent No.: US 10,405,781 B2
(45) Date of Patent: Sep. 10, 2019

(54) MOBILE DEVICE, MOVEMENT STATE DETECTION METHOD, AND NON-TRANSITORY STORAGE MEDIUM STORING MOVEMENT STATE DETECTION PROGRAM

(71) Applicant: KYOCERA Corporation, Kyoto-shi, Kyoto (JP)

(72) Inventors: Shigeki Tanabe, Yokohama (JP); Hideki Morita, Yokohama (JP); Isao Masuike, Machida (JP); Shinya Saito, Kawasaki (JP)

(73) Assignee: KYOCERA CORPORATION, Kyoto (JP)

( * ) Notice: Subject to any disclaimer, the term of this patent is extended or adjusted under 35 U.S.C. 154(b) by 330 days.

(21) Appl. No.: 15/221,540

(22) Filed: Jul. 27, 2016

(65) Prior Publication Data
US 2017/0027478 A1    Feb. 2, 2017

(30) Foreign Application Priority Data

Jul. 28, 2015 (JP) .................. 2015-148917
Sep. 29, 2015 (JP) .................. 2015-191545

(51) Int. Cl.
| | | |
|---|---|---|
| A61B 5/11 | (2006.01) | |
| A61B 5/00 | (2006.01) | |
| G01C 22/00 | (2006.01) | |
| G06K 9/00 | (2006.01) | |
| G01C 5/06 | (2006.01) | |

(52) U.S. Cl.
CPC .......... *A61B 5/1123* (2013.01); *A61B 5/1126* (2013.01); *A61B 5/6898* (2013.01); *A61B 5/7278* (2013.01); *G01C 22/006* (2013.01); *G06K 9/00348* (2013.01); *A61B 2560/0257* (2013.01); *G01C 5/06* (2013.01)

(58) Field of Classification Search
CPC .................................................... A61B 5/1123
See application file for complete search history.

(56) References Cited

U.S. PATENT DOCUMENTS

2007/0072158 A1    3/2007 Unuma et al.
2014/0195018 A1    7/2014 Kang et al.

FOREIGN PATENT DOCUMENTS

| EP | 1770370 A2 | 4/2007 |
| JP | 2007-93433 A | 4/2007 |

(Continued)

OTHER PUBLICATIONS

Office Action in JP Application No. 2015-191545, dated May 9, 2017, for which an explanation of relevance is attached.

(Continued)

*Primary Examiner* — Daniel L Cerioni
*Assistant Examiner* — Yasmeen S Warsi
(74) *Attorney, Agent, or Firm* — Hauptman Ham, LLP

(57) ABSTRACT

A mobile device comprises an air pressure sensor configured to measure a value of air pressure, a walk detector configured to detect whether a user is walking, and a controller configured to estimate a movement method of the user using an own device based on results of the air pressure sensor and the walk detector, wherein in a case where a change amount of the value of the air pressure detected by the air pressure sensor is equal to or larger than a reference value and the walk detector detects that the user is walking, the controller estimates that the user is moving on stairs.

8 Claims, 9 Drawing Sheets

(56) References Cited

FOREIGN PATENT DOCUMENTS

| JP | 2009-267770 A | 11/2009 |
| JP | 2009-281741 A | 12/2009 |
| JP | 2012-237719 A | 12/2012 |
| JP | 2014-192735 A | 10/2014 |

OTHER PUBLICATIONS

Takafumi Watanabe et al., "A Study on Locomotion Estimation Using Pressure Sensor", Proccedings of the 2011 IEICE General Conference, Mar. 18, 2011, p. 609, The Institute of Electronics, Information and Communication Engineers, Japan.
Partial European Search Report in EP Application No. 16181522.0, dated Jan. 30, 2017.

TIME [h]

TIME [min]

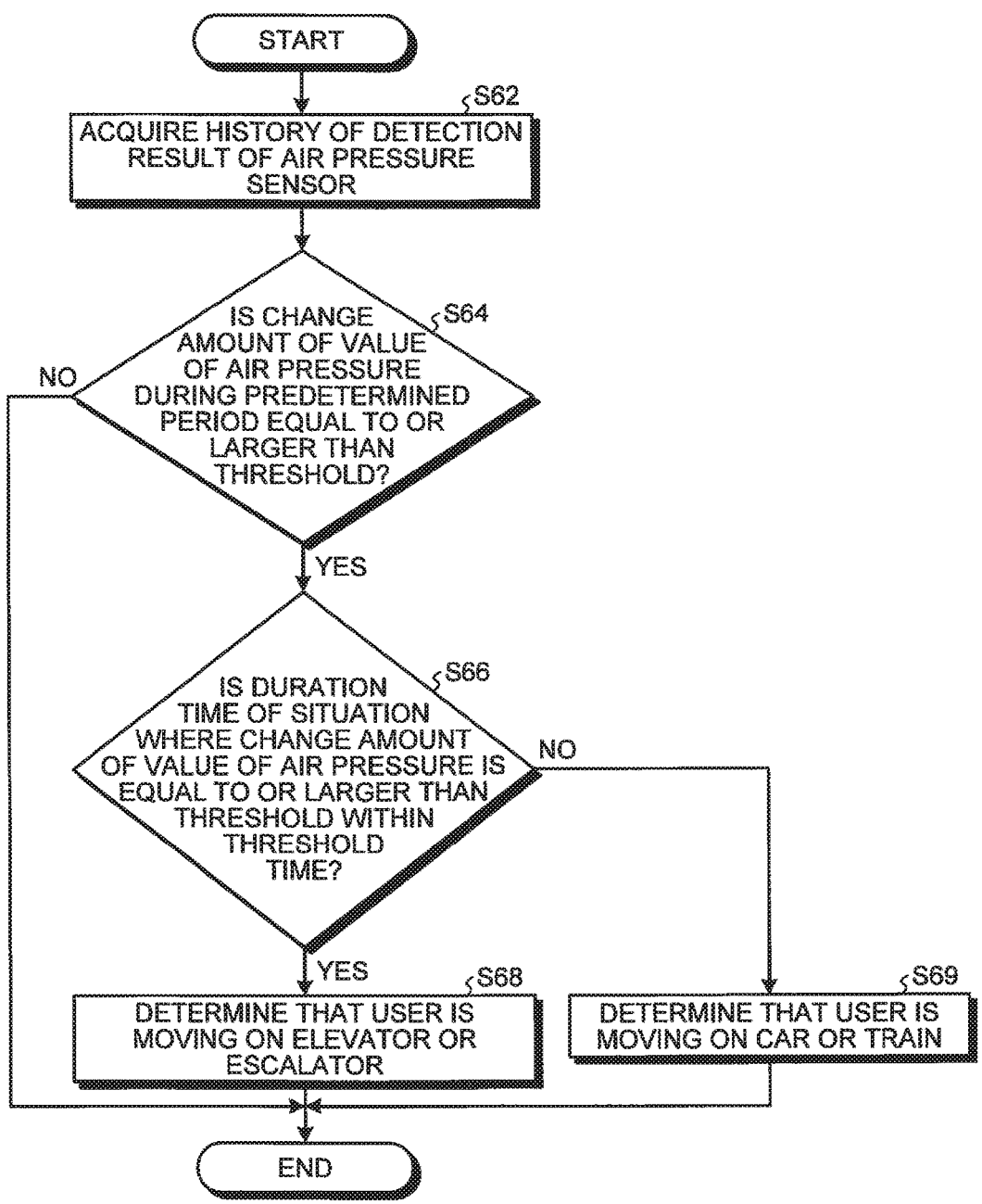

MOBILE DEVICE, MOVEMENT STATE DETECTION METHOD, AND NON-TRANSITORY STORAGE MEDIUM STORING MOVEMENT STATE DETECTION PROGRAM

CROSS-REFERENCE TO RELATED APPLICATION

The present application claims priority to and incorporates by reference the entire contents of Japanese Patent Application No. 2015-191545 filed in Japan on Sep. 29, 2015 and Japanese Patent Application No. 2015-148917 filed in Japan on Jul. 28, 2015.

BACKGROUND

1. Field

The present application relates to a mobile device, a movement state detection method, and a movement state detection program.

2. Description of the Related Art

Some mobile devices used as mobile communication devices are capable of determining whether to be moving. For example, Japanese Laid-open Patent Publication No. 2009-267770 A discloses a technique for determining the movement on a conveyance such as a train based on a detection result of an acceleration sensor. Japanese Laid-open Patent Publication No. 2012-237719 A describes that a vertical movement state is detected based on a detection result of an air pressure sensor.

Patent Literature 1: Japanese Laid-open Patent Publication No. 2009-267770 A Patent Literature 2: Japanese Laid-open Patent Publication No. 2012-237719 A A mobile device capable of detecting various types of movement states can extend various types of functions. However, a larger processing load due to the detection of movement state affects other functions in some cases. A larger processing load due to the detection of movement state can reduce a usable time of an apparatus.

Because of the situation described above, there is a need for a mobile device, a movement state detection method, and a movement state detection program capable of accurately categorizing movement modes to detect through a lighter processing load.

SUMMARY

It is an object of the present invention to at least partially solve the problems in the conventional technology.

According to one aspect, there is provided a mobile device comprising:

an air pressure sensor configured to measure a value of air pressure;

a walk detector configured to detect whether a user is walking; and a controller configured to estimate a movement method of the user using an own device based on results of the air pressure sensor and the walk detector, wherein in a case where a change amount of the value of the air pressure detected by the air pressure sensor is equal to or larger than a reference value and the walk detector detects that the user is walking, the controller estimates that the user is moving on stairs.

According to one aspect, there is provided a mobile device comprising:

an air pressure sensor configured to measure a value of air pressure;

a walk detector configured to detect whether a user is walking; and a controller configured to estimate a movement method of the user using an own device based on results of the air pressure sensor and the walk detector, wherein when a change amount of the value of the air pressure detected by the air pressure sensor is equal to or larger than a reference value and the walk detector does not detect that the user is walking, the controller estimates that the user is moving on an escalator in a case where the user is detected to be walking for a predetermined distance while the air pressure is not changing or direction switching is detected, and in the other cases, the controller determines that the user is moving on an elevator.

According to one aspect, there is provided a mobile device comprising:

an air pressure sensor configured to measure a value of air pressure;

a walk detector configured to detect whether a user is walking; and a controller configured to estimate a movement method of the user using an own device based on results of the air pressure sensor and the walk detector, wherein in a case where a change amount of the value of the air pressure detected by the air pressure sensor is equal to or larger than a reference value and the walk detector detects that the user is walking, the controller estimates that the user is moving on stairs or a hill, and in a case where the change amount of the value of the air pressure detected by the air pressure sensor is equal to or larger than the reference value and the walk detector detects that the user is not walking, the controller estimates that the user is moving on an elevator or an escalator.

According to one aspect, there is provided mobile device comprising:

an air pressure sensor configured to measure a value of air pressure; and a controller configured to estimate a movement method of the user using an own device based on a result of the air pressure sensor, wherein in a case where a change amount of the value of the air pressure detected by the air pressure sensor is equal to or larger than a reference value and a period during which the air pressure is changing is detected to be within a threshold period, the controller estimates that the user is moving on an elevator or an escalator.

According to one aspect, there is provided a movement state detection method configured to control a mobile device including an air pressure sensor that measures a value of air pressure and a walk detector that detects whether a user is walking, comprising:

a step of estimating whether the user is walking;

a step of detecting the value of the air pressure based on the air pressure sensor; and a step of estimating that the user is moving on stairs in a case where a change amount of the value of the air pressure detected by the air pressure sensor is equal to or larger than a reference value and the walk detector detects that the user is walking.

According to one aspect, there is provided a non-transitory storage medium that stores a movement state detection program for causing a mobile device including an air pressure sensor configured to measure a value of air pressure and a walk detector configured to detect whether a user is walking to execute:

a step of estimating whether the user is walking;

a step of detecting the value of the air pressure based on the air pressure sensor; and a step of estimating that the user is moving on stairs in a case where a change amount of the value of the air pressure detected by the air pressure sensor is equal to or larger than a reference value and the walk detector detects that the user is walking.

The above and other objects, features, advantages and technical and industrial significance of this invention will be better understood by reading the following detailed description of presently preferred embodiments of the invention, when considered in connection with the accompanying drawings.

BRIEF DESCRIPTION OF THE DRAWINGS

FIG. 12 is a flowchart illustrating exemplary control carried out by the smartphone according to embodiments.

DETAILED DESCRIPTION OF THE PREFERRED EMBODIMENTS

Embodiments for carrying out the present invention will be described in detail with reference to the drawings. A smartphone will be described hereinafter as an example of an apparatus provided with a touch screen.

Figure 1:
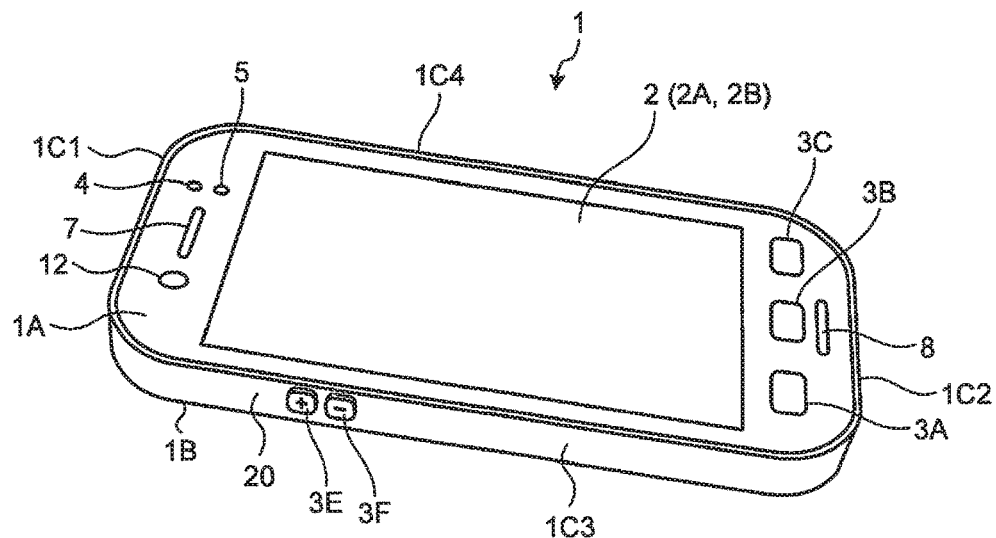
FIG. 1 is a perspective view of a smartphone according to embodiments.
Figure 2:
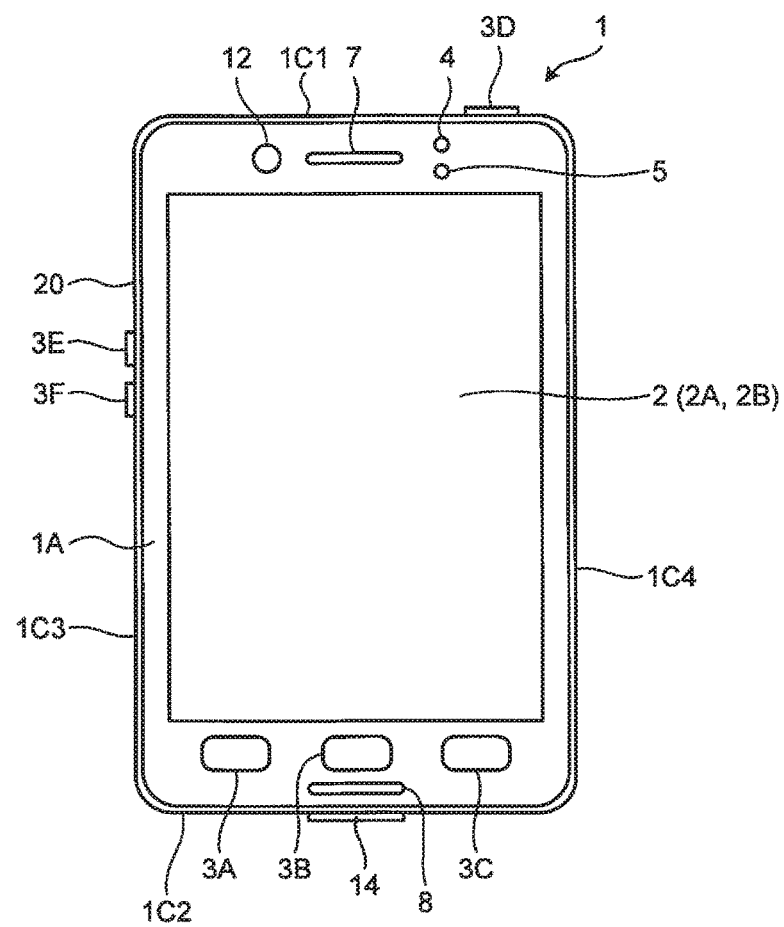
FIG. 2 is a front view of the smartphone.
Figure 3:
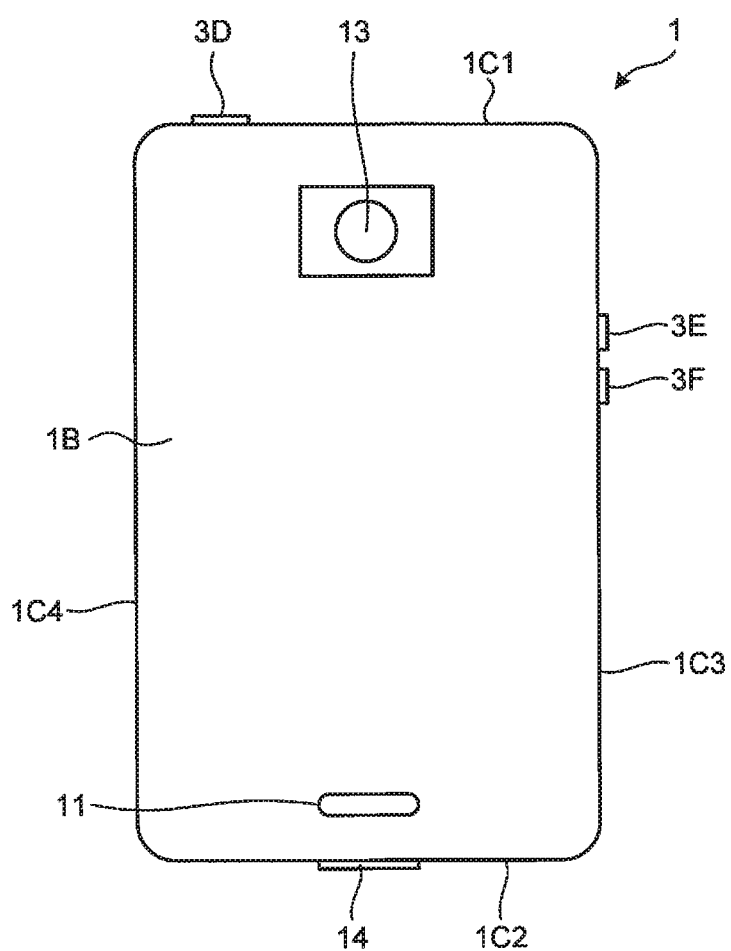
FIG. 3 is a rear view of the smartphone.

An overall configuration of a smartphone 1 according to embodiments will be described with reference to FIG. 1 to FIG. 3. As illustrated in FIG. 1 to FIG. 3, the smartphone 1 includes a housing 20. The housing 20 includes a front face 1A, a back face 1B, and side faces 1C1 to 1C4. The front face 1A serves as a front surface of the housing 20. The back face 1B serves as a rear surface of the housing 20. The side faces 1C1 to 1C4 serve as lateral surfaces connecting the front face 1A and the back face 1B. Hereinafter, the side faces 1C1 to 1C4 are generically referred to as side faces 1C in some cases without identifying which specific surface is meant.

The smartphone 1 includes, in the front face 1A, a touch screen display 2, buttons 3A to 3C, an illuminance sensor 4, a proximity sensor 5, a receiver 7, a microphone 8, and a camera 12. The smartphone 1 includes a speaker 11 and a camera 13 in the back face 1B. The smartphone 1 includes buttons 3D to 3F and a connector 14 in the side faces 1C. Hereinafter, the buttons 3A to 3F are generically referred to as buttons 3 in some cases without identifying which specific button is meant.

The touch screen display 2 includes a display 2A and a touch screen 2B. Both of the display 2A and the touch screen 2B have substantially rectangular shapes in the example in FIG. 1. However, the shapes of the display 2A and the touch screen 2B are not limited thereto. Each of the display 2A and the touch screen 2B may have any shape such as a square shape or a circular shape. The display 2A and the touch screen 2B are positioned so as to overlap in the example in FIG. 1. However, the positions of the display 2A and the touch screen 2B are not limited thereto. For example, the display 2A and the touch screen 2B may be positioned side by side or away from each other. In the example in FIG. 1, long sides of the display 2A are along long sides of the touch screen 2B, whereas short sides of the display 2A are along short sides of the touch screen 2B. However, how the display 2A and the touch screen 2B overlap is not limited thereto. In a case where the display 2A and the touch screen 2B are positioned so as to overlap, for example, one side or a plurality of sides of the display 2A may not be along any side of the touch screen 2B.

The display 2A includes a display device such as a liquid crystal display (LCD), an organic electro-luminescence display (OELD), or an inorganic electro-luminescence display (IELD). The display 2A displays a text, an image, a symbol, a figure, and other objects.

The touch screen 2B detects contact or proximity with the touch screen 2B by a finger, a pen, a stylus pen, or the like. The touch screen 2B is capable of detecting positions on the touch screen 2B with which a plurality of fingers, pens, stylus pens, or the like makes contact. In the following description, a finger, a pen, a stylus pen, or the like that makes contact with the touch screen 2B is also referred to as "contact object" or "contact item". The action that the touch screen 2B is capable of carrying out can be carried out by the touch screen display 2 including the touch screen 2B. In other words, the action carried out by the touch screen 2B may be carried out by the touch screen display 2.

A detection method of the touch screen 2B may be any method such as an electrostatic capacitance method, a resistive film method, a surface acoustic wave method, an infrared method, and a load detection method. For a simple description, the following description assumes that a user makes contact with the touch screen 2B with his/her finger to operate the smartphone 1.

A controller 10 distinguishes the classifications of gestures based on at least one of contact or proximity detected by the touch screen 2B, a position at which contact is detected, a change in a position at which contact is detected, a time during which contact or proximity continues, a time interval at which contact or proximity is detected, and the number of times contact is detected. The touch screen 2B may distinguish these gestures. The controller 10 may work in coordination with the touch screen 2B to distinguish these gestures. The action that the controller 10 is capable of carrying out can be carried out by the smartphone 1 including the controller 10. In other words, the action carried out by the controller 10 may be carried out by the smartphone 1. A gesture is operation carried out on the touch screen 2B. Examples of the gestures distinguished by the smartphone 1 include, but are not limited to, a touch, a long touch, a release, a swipe, a tap, a double tap, a long tap, a drag, a flick, a pinch in, a pinch out, etc.

Figure 4:
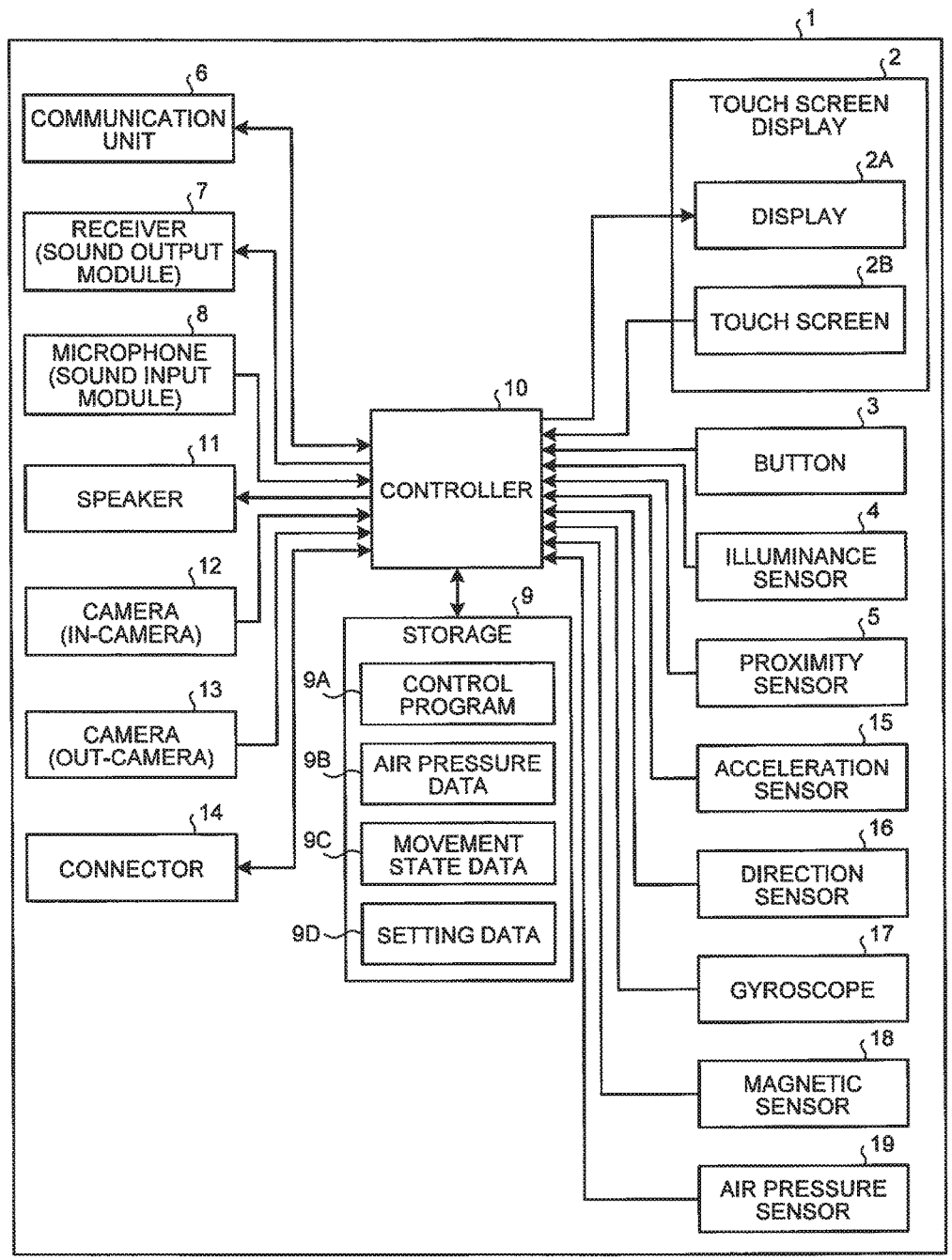
FIG. 4 is a block diagram of the smartphone.

FIG. 4 is a block diagram of the smartphone 1. The smartphone 1 includes the touch screen display 2, the buttons 3, the illuminance sensor 4, the proximity sensor 5, a communication unit 6, the receiver 7, the microphone 8, a storage 9, the controller 10, the speaker 11, the cameras 12 and 13, the connector 14, an acceleration sensor 15, a direction sensor 16, a gyroscope 17, a magnetic sensor 18, and an air pressure sensor 19.

As described above, the touch screen display 2 includes the display 2A and the touch screen 2B. The display 2A displays a text, an image, a symbol, a figure, or the like. The touch screen 2B detects contact. The controller 10 detects a gesture on the smartphone 1. Specifically, the controller 10 works in coordination with the touch screen 2B to detect operation (gesture) on the touch screen 2B (touch screen display 2).

The buttons 3 are operated by the user. The buttons 3 include the button 3A to the button 3F. The controller 10 works in coordination with the buttons 3 to detect operation on the buttons 3. Examples of the operation on the buttons 3 include, but are not limited to, a click, a double click, a triple click, a push, a multiple push, etc.

The buttons 3A to 3C are, for example, a home button, a back button, and a menu button. The button 3D is, for example, a power on/off button of the smartphone 1. The button 3D may also function as a sleep/wake-up button. The buttons 3E and 3F are, for example, volume buttons.

The illuminance sensor 4 detects illuminance of surrounding light of the smartphone 1. The illuminance represents intensity of light, brightness, or luminance. The illuminance sensor 4 is used to, for example, adjust the luminance of the display 2A. The proximity sensor 5 detects a presence of an object in the vicinity thereof without contact. The proximity sensor 5 detects a presence of an object based on, for example, a change in a magnetic field or a change in a time required for a reflected wave of an ultrasonic wave to return. For example, the proximity sensor 5 detects that the touch screen display 2 has been moved closer to a face. The illuminance sensor 4 and the proximity sensor 5 may be configured as a single sensor. The illuminance sensor 4 may be used as a proximity sensor.

The communication unit 6 wirelessly communicates. A communication method supported by the communication unit 6 is a wireless communication standard. Examples of the wireless communication standards include communication standards for cellular phones such as 2G, 3G, and 4G. Examples of the communication standards for cellular phones include the long term evolution (LTE), the wideband code division multiple access (W-CDMA), CDMA2000, the personal digital cellular (PDC), the Global System for Mobile Communications (GSM) (registered trademark), and the personal handy-phone system (PHS). Additional examples of the wireless communication standards include the worldwide interoperability for microwave access (WiMAX), IEEE802.11, Bluetooth (registered trademark), the infrared data association (IrDA), and the near field communication (NFC). The communication unit 6 may support one or a plurality of the aforementioned communication standards. The communication unit 6 may support wired communication. Examples of the wired communication include Ethernet (registered trademark) and the fiber channel.

The receiver 7 and the speaker 11 are sound output modules. The receiver 7 and the speaker 11 output tone signals transmitted from the controller 10 as sounds. The receiver 7 is used to, for example, output a voice of a person the user is talking with during the telephone conversation. The speaker 11 is used to, for example, output a ringtone and music. One of the receiver 7 and the speaker 11 may have a function of the other. The microphone 8 is a sound input module. The microphone 8 converts a voice of the user or the like to a tone signal to transmit to the controller 10.

The storage 9 stores a program and data. The storage 9 is also used as a working area temporarily storing a processing result of the controller 10. The storage 9 may include any non-transitory storage medium such as a semiconductor storage medium or a magnetic storage medium. The storage 9 may include a plurality of types of storage media. The storage 9 may include a combination of a transportable storage medium such as a memory card, an optical disc, or a magneto-optical disk and a reading apparatus for the storage medium. The storage 9 may include a storage device used as a temporary storage area such as a random access memory (RAM).

Programs stored in the storage 9 include an application executed in foreground or background and a control program that assists the action of the application. For example, the application causes the display 2A to display a screen and the controller 10 to carry out processing in accordance with a gesture detected through the touch screen 2B. The control program is, for example, an OS. The application and the control program may be installed in the storage 9 through the communication via the communication unit 6 or a non-transitory storage medium.

The storage 9 stores, for example, a control program 9A, air pressure data 9B, movement state data 9C, and setting data 9D. The air pressure data 9B includes information on a relationship between the detection result of the air pressure sensor 19 and the state of the smartphone 1. The air pressure data 9B stores a relationship between the detection result of the air pressure sensor 19 and a change in height, which has been detected in advance through a test, a simulation, or the like. The movement state data 9C includes information used to estimate a movement method of the user. The movement state data 9C stores a corresponding relationship between the detection result of a sensor and a movement method, which has been detected in advance through a test, a simulation, or the like. The setting data 9D includes information on various types of settings relating to the action of the smartphone 1.

The control program 9A provides functions relating to various types of control for causing the smartphone 1 to operate. For example, the control program 9A controls the communication unit 6, the receiver 7, and the microphone 8 to realize the telephone conversation. The functions provided by the control program 9A include functions that carry out various types of control such as the modification of the information being displayed on the display 2A in accordance with a gesture detected through the touch screen 2B. The functions provided by the control program 9A are used in some cases in combination with a function provided by another program such as a mail application.

The controller 10 is a computational processing unit. Examples of the computational processing units include, but are not limited to, a central processing unit (CPU), a system-on-a-chip (SoC), a micro control unit (MCU), a field-programmable gate array (FPGA), etc. The controller 10 integrally controls the action of the smartphone 1 to realize various types of functions.

Specifically, the controller 10 executes an instruction included in a program stored in the storage 9 while referring to data stored in the storage 9 as necessary. The controller 10 then controls a function module in accordance with the data and the instruction to thereby realize various types of functions. For example, the function module may include at least one of the display 2A, the communication unit 6, the receiver 7, and the speaker 11. However, the function module is not limited thereto. The controller 10 changes the control in some cases depending on the detection result of a detector. For example, the detector may include at least one of the touch screen 2B, the buttons 3, the illuminance sensor 4, the proximity sensor 5, the microphone 8, the camera 12, the camera 13, the acceleration sensor 15, the direction sensor 16, the gyroscope 17, the magnetic sensor 18, and the air pressure sensor 19. However, the detector is not limited thereto.

For example, the controller 10 executes the control program 9A to carry out various types of control such as the modification of the information being displayed on the display 2A in accordance with a gesture detected through the touch screen 2B.

The camera 12 is an in-camera that images an object facing the front face 1A. The camera 13 is an out-camera that images an object facing the back face 1B.

The connector 14 is a terminal to which another apparatus is connected. The connector 14 may be a general-purpose terminal such as the universal serial bus (USB), the High-Definition Multimedia Interface (HDMI) (registered trademark), Light Peak (Thunderbolt (registered trademark)), and an earphone microphone connector. The connector 14 may be a dedicated terminal such as a Dock connector. Examples of the apparatuses connected to the connector 14 include, but are not limited to, an external storage, a speaker, a communication apparatus, etc.

The acceleration sensor 15 detects the direction and the degree of the acceleration applied to the smartphone 1. The direction sensor 16 detects the direction of geomagnetism. The gyroscope 17 detects the angle and the angular velocity of the smartphone 1. The magnetic sensor 18 detects the magnetic force around the smartphone 1. The air pressure sensor 19 detects the air pressure (atmospheric pressure) at the outside of the smartphone 1. The air pressure sensor 19 is positioned inside the housing 20. The air pressure is continuous between the inside and the outside of the housing 20 through a hole allowing the air to pass but not allowing the water to pass. Accordingly, the air pressure sensor 19 can detect the air pressure at the outside of the smartphone 1 while being positioned at the inside thereof. The detection results of the acceleration sensor 15, the direction sensor 16, and the gyroscope 17 are combined when used to detect changes in the position and the attitude of the smartphone 1.

Part or all of the programs and the data stored in the storage 9 in FIG. 4 may be downloaded from another apparatus through the communication via the communication unit 6. Part or all of the programs and the data stored in the storage 9 in FIG. 4 may be stored in a non-transitory storage medium readable by a reading apparatus included in the storage 9. Part or all of the programs and the data stored in the storage 9 in FIG. 4 may be stored in a non-transitory storage medium readable by a reading apparatus connected to the connector 14. Examples of the non-transitory storage media include, but are not limited to, the optical disc such as CD (registered trademark), DVD (registered trademark), and Blu-ray (registered trademark), the magneto-optical disk, the magnetic storage medium, the memory card, the solid state storage medium, etc.

The configuration of the smartphone 1 illustrated in FIG. 4 is an example and may be modified as appropriate without deviating from the spirit of the invention. For example, the number and the types of the buttons 3 are not limited to the example in FIG. 4. Instead of the buttons 3A to 3C, the smartphone 1 may be provided with buttons, for example, in a numeric key arrangement or a QWERTY arrangement as buttons for the operation relating to the screen. The smartphone 1 may be provided with only a single button for the operation relating to the screen, or alternatively, may be provided with no button. In the example illustrated in FIG. 4, the smartphone 1 is provided with two cameras. However, the smartphone 1 may be provided with only a single camera, or alternatively, may be provided with no camera. In the example illustrated in FIG. 4, the smartphone 1 is provided with the three types of sensors for detecting the position and the attitude thereof. However, the smartphone 1 may not be provided with several sensors among these sensors. Alternatively, the smartphone 1 may be provided with another type of sensor for detecting at least one of the position and the attitude thereof.

Figure 5:
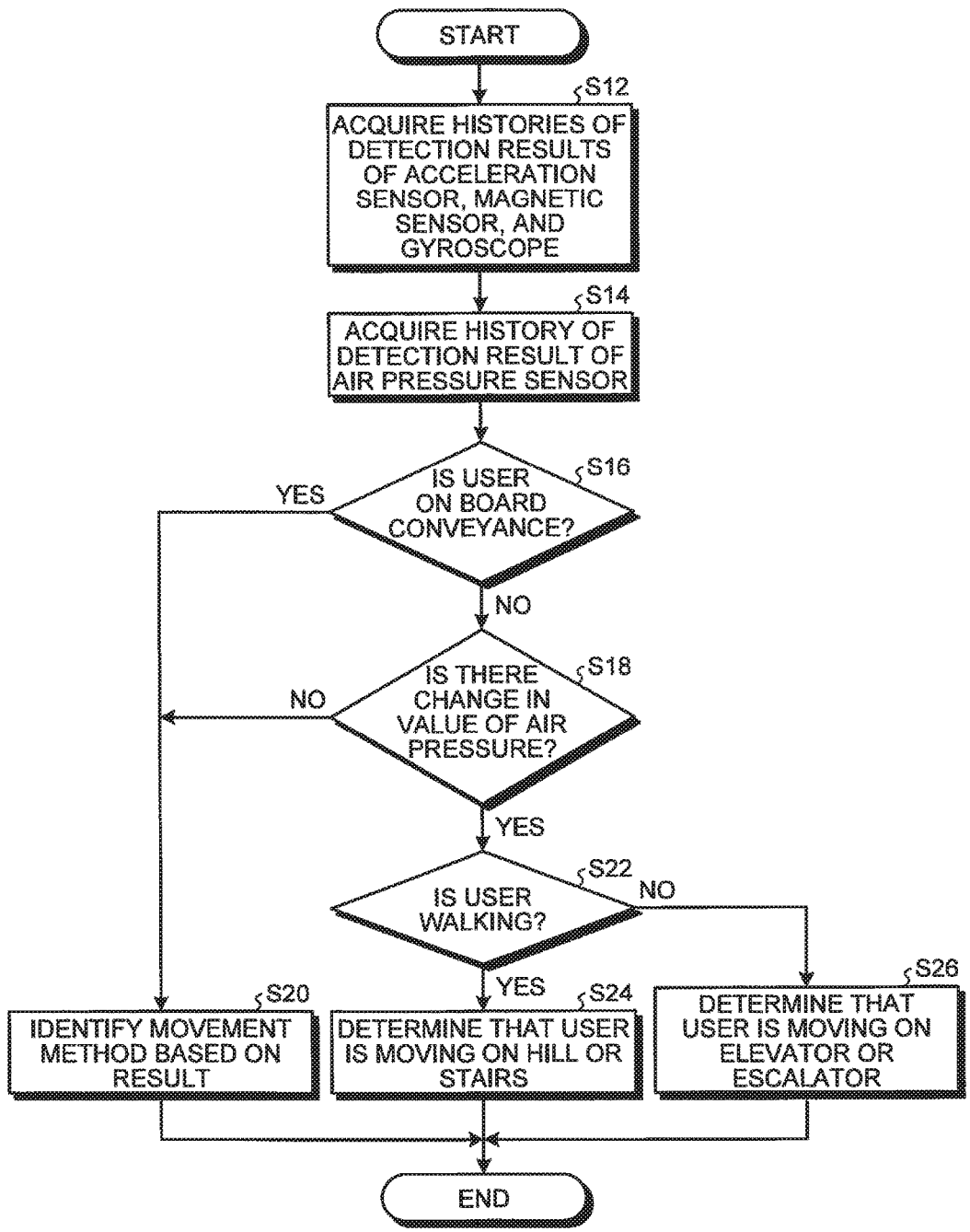
FIG. 5 is a flowchart illustrating exemplary control carried out by the smartphone according to embodiments.
Figure 6:
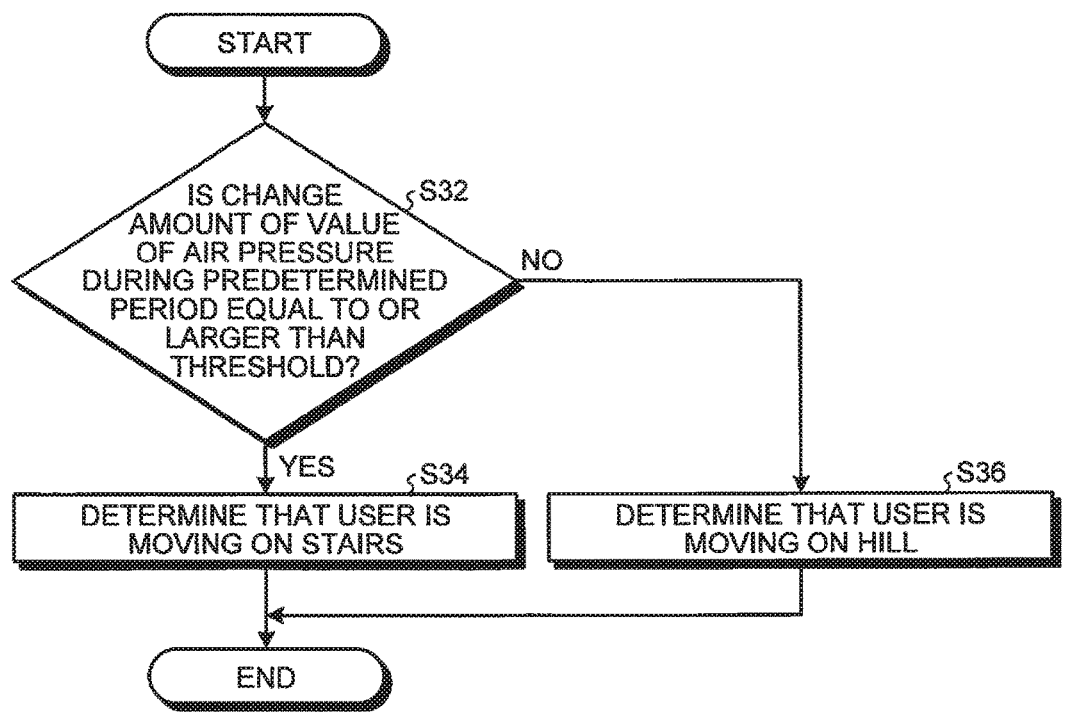
FIG. 6 is a flowchart illustrating exemplary control carried out by the smartphone according to embodiments.
Figure 7:
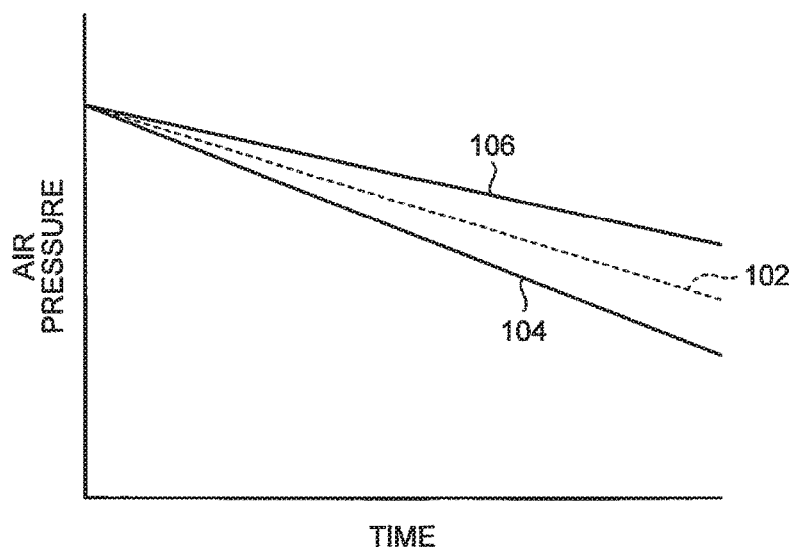
FIG. 7 is a graph illustrating an exemplary detection result of an air pressure sensor.
Figure 8:
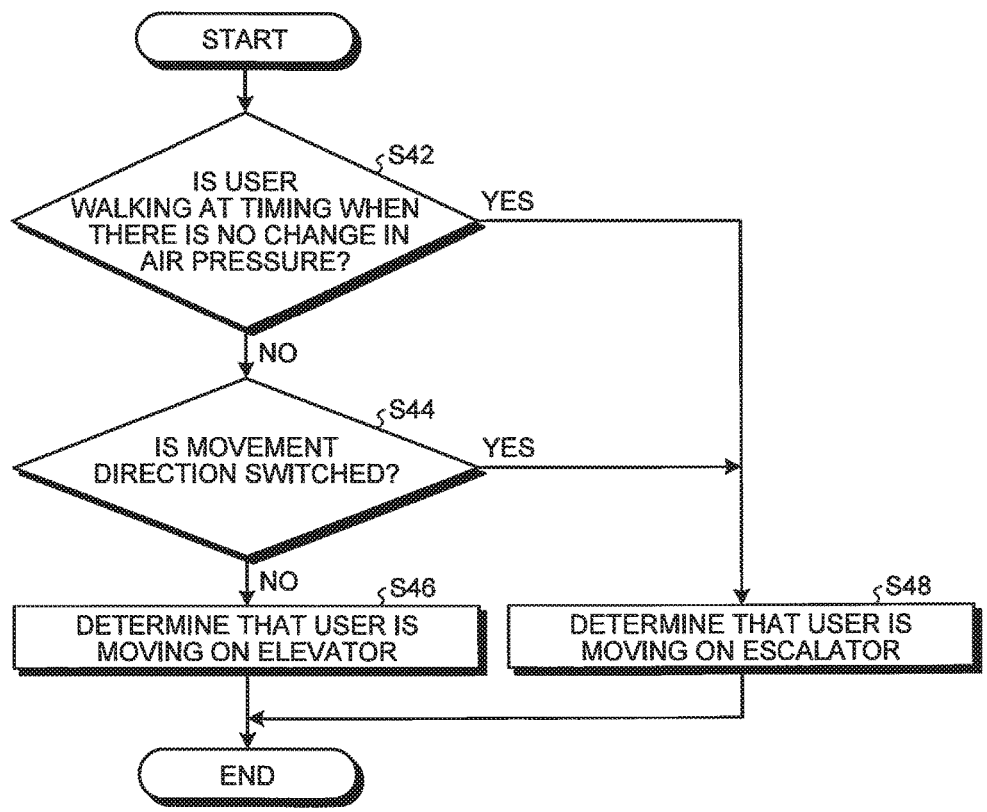
FIG. 8 is a flowchart illustrating exemplary control carried out by the smartphone according to embodiments.
Figure 9:
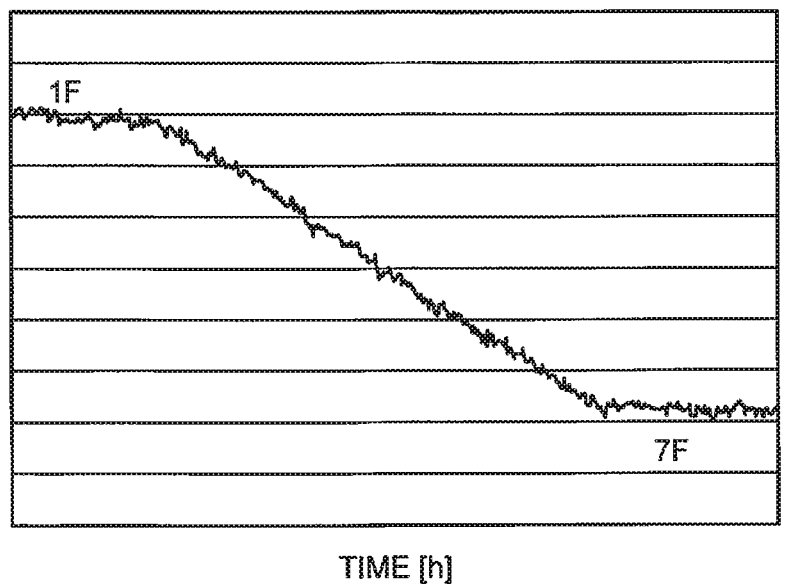
FIG. 9 is a graph illustrating an exemplary detection result of the air pressure sensor.
Figure 10:
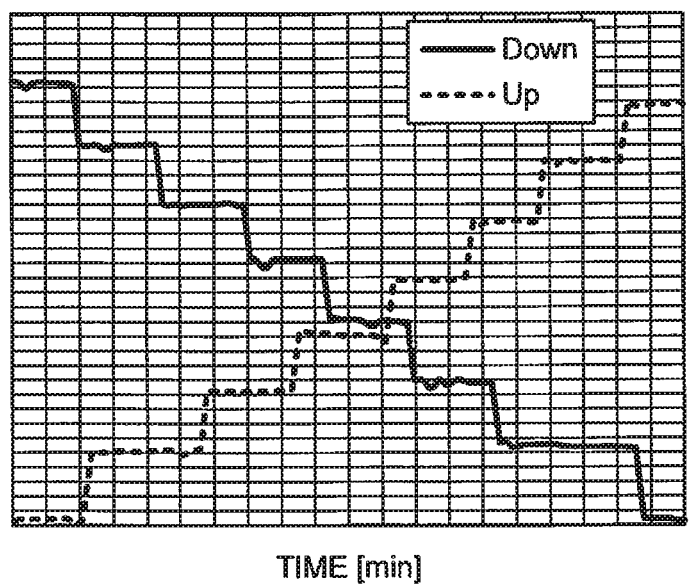
FIG. 10 is a graph illustrating an exemplary detection result of the air pressure sensor.
Figure 11:
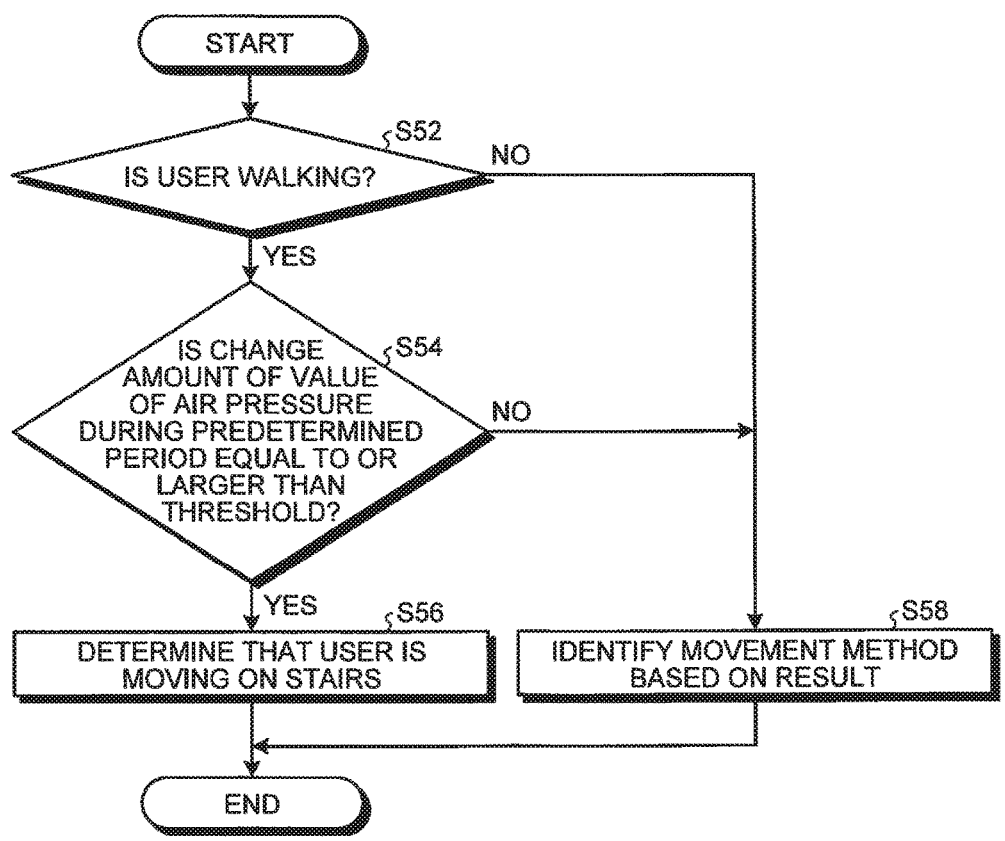
FIG. 11 is a flowchart illustrating exemplary control carried out by the smartphone according to embodiments.

Then, the control carried out by the smartphone 1 will be described with reference to FIG. 5 to FIG. 11. Each of FIG. 5 and FIG. 6 is a flowchart illustrating exemplary control carried out by the smartphone according to embodiments. FIG. 7 is a graph illustrating an exemplary detection result of the air pressure sensor. FIG. 8 is a flowchart illustrating exemplary control carried out by the smartphone according to embodiments. Each of FIG. 9 and FIG. 10 is a graph illustrating an exemplary detection result of the air pressure sensor. FIG. 11 is a flowchart illustrating exemplary control carried out by the smartphone according to embodiments.

First of all, overall processing carried out by the smartphone 1 during the determination of the movement state will be described with reference to FIG. 5. The smartphone 1 is capable of realizing a function illustrated in FIG. 5 by executing the control program 9A stored in the storage 9 using the controller 10. The controller 10 in some cases carries out a processing procedure for another function in parallel to the processing procedure illustrated in FIG. 5.

First of all, the controller 10 acquires histories of the detection results of the acceleration sensor 15, the magnetic sensor 18, and the gyroscope 17 at Step S12. The histories of the detection results of the acceleration sensor 15, the magnetic sensor 18, and the gyroscope 17 are used to determine the movement state, specifically, whether the user is on board a conveyance, what conveyance the user is on board, and the like. The controller 10 may acquire, as information used to estimate the movement state, a history of a detection result of a sensor other than the detection results of the acceleration sensor 15, the magnetic sensor 18, and the gyroscope 17. Subsequently, the controller 10 of the smartphone 1 acquires a history of the detection result of the air pressure sensor 19 at Step S14. The controller 10 acquires a value of the air pressure from the detection result of the air pressure sensor 19. The controller 10 may change the order of the processing at Step S12 and Step S14 to a different order, or alternatively, may carry out the processing in parallel.

When the respective types of information have been acquired through the processing at Step S12 and Step S14, the controller 10 determines whether the user is on board a conveyance at Step S16. The conveyances include a bicycle, a motorcycle, a car, a train, an amphibious vehicle, a vessel, and a plane. The movement state data 9C stores various types of ranges and thresholds for determining the movement state. For example, in a case where the movement method is estimated based on the acceleration, ranges of the amplitude and the cycle of the acceleration are set for each of the movement states. The controller 10 uses the range and the threshold set in the movement state data 9C and the value detected at Step S12 to estimate the movement state. The movement state has a possibility of occurring due to temporary shaking of a terminal when determined based on a short time. Accordingly, it is preferable for the controller 10 to acquire the history for a certain time and determine the movement state in accordance with whether a condition is continuously satisfied during the certain time. With this, the accuracy of the estimation can be enhanced. In a case where the user is not on board a conveyance, the controller 10 determines that the movement method is the movement on the feet of the user. The movement on the feet of the user represents a state where the user carrying the smartphone 1 moves him/herself, that is, a state where the user moves without taking a conveyance that assists the user to move. The movement on the feet of the user includes at least one of a walk, that is, a state during walking and a run, that is, a state during running. The movement on the feet of the user also includes a state while the user stays still without moving on his/her feet. Additionally, the movement on the feet of the user includes walking with a stick, a pushcart, or the like.

When it is determined that the user is on board a conveyance (Yes at Step S16), the controller 10 proceeds to Step S20. When it is determined that the user is not on board a conveyance (No at Step S16), that is, it is determined that the user is moving on his/her feet, the controller 10 determines whether there is a change in the air pressure at Step S18. A change in a value of the air pressure is determined based on a threshold set in advance in the air pressure data 9B. The threshold is set as a value of the air pressure changed per a set period. When the value of the air pressure changed per the set period is equal to or larger than the threshold, the controller 10 determines that there is a change in the air pressure. When the value of the air pressure changed per the set period is smaller than the threshold, the controller 10 determines that there is no change in the air pressure. Examples of the period serving as a reference for the threshold include a time and a counter based on a clock.

When it is determined that there is no change in the air pressure (No at Step S18), the controller 10 proceeds to Step S20. When it is determined that the user is on board a conveyance (Yes at Step S16), and when it is determined that there is no change in the air pressure (No at Step S18), the controller 10 identifies the movement method based on the result at Step S20. Specifically, when it is determined that the user is on board a conveyance, the controller 10 identifies the conveyance which the user is on board based on at least one of the histories of the information among the acceleration, the magnetism, and the direction to determine that the user is moving on the identified conveyance. When it is determined that the user is not on board a conveyance and there is no change in the air pressure, the controller 10 determines that the user is moving on his/her feet on a flat road.

Subsequently, when it is determined that there is a change in the air pressure (Yes at Step S18), the controller 10 determines whether the user is walking at Step S22. Although some embodiments determine whether the user is walking, whether the user is moving on his/her feet may be determined. Specifically, it may be determined whether the user is moving on his/her feet and whether the user is standing or sitting without moving his/her feet.

When it is determined that the user is walking (Yes at Step S22), the controller 10 determines that the user is moving on a hill or stairs at Step S24. When it is determined that the user is not walking (No at Step S22), the controller 10 determines that the user is moving on an elevator or an escalator at Step S26.

By using the determination on whether the user is walking and the result of the air pressure sensor, the smartphone 1 is capable of determining whether the user is moving on a hill or stairs or moving on an elevator or an escalator. As a result, the movement modes can be accurately categorized to be detected through a lighter processing load. It is preferable to use the result of the acceleration sensor for the movement state and the determination on whether the user is walking. The smartphone 1 first detects whether the user is on board a conveyance. When the user is not on board a conveyance, the smartphone 1 determines whether the user is moving on an elevator or an escalator. Accordingly, it can be avoided to falsely detect a state where the user is on board a conveyance as moving on an elevator or an escalator.

The smartphone 1 uses the change in the air pressure during the certain time for the determination of the change in the air pressure, thereby being capable of determining whether the change in the air pressure is due to a climate change or the change is due to the movement. For example, the air pressure also varies while the terminal stays still not during walking. However, by setting the certain time, variations in the air pressure unlikely to occur due to a usual change in the atmospheric pressure can be determined as due to an elevator or an escalator when such variations are observed.

In the processing illustrated in FIG. 5, a case where there is a change in the air pressure and the user is walking has been determined as that the user is moving on a hill or stairs. It is preferable for the smartphone 1 to further determine whether the user is moving on a hill or moving on stairs based on the detection result of the air pressure sensor.

Another example of the processing carried out at Step S24 will be described with reference to FIG. 6 and FIG. 7. The controller 10 determines whether a change amount of a value of the air pressure during a predetermined period is equal to or larger than a threshold at Step S32. The threshold at Step S32 has a larger change amount of the value of the air pressure per time than that of the threshold used for the determination at Step S18 in FIG. 5.

When it is determined that the change amount of the value of the air pressure is equal to or larger than the threshold (Yes at Step S32), the controller 10 determines that the user is moving on stairs at Step S34. When it is determined that the change amount of the value of the air pressure is smaller than the threshold (No at Step S32), the controller 10 determines that the user is moving on a hill at Step S36. FIG. 7 illustrates an example of moving toward a higher side in height. As illustrated in FIG. 7, a threshold 102 is set for the change amount of the value of the air pressure per time. When the change amount of the value of the air pressure is equal to or larger than the threshold 102 as indicated by a line segment 104 illustrated in FIG. 7, the controller 10 determines that the user is moving on stairs. When the change amount of the value of the air pressure is smaller than the threshold 102 as indicated by a line segment 106 illustrated in FIG. 7, the controller 10 determines that the user is moving on a hill.

As described above, the threshold for the change in the air pressure per time is used for the determination between a hill and stairs. As a result, it is possible to accurately determine whether the user is moving on a hill or moving on stairs. In the case of stairs, 20 stairsteps (walking steps) are required to go up a height of one floor (approximately three meters) on average. As for a time required therefor, even assuming that going up one stairstep requires one second, going up three meters can be completed in 20 seconds. In contrast to this, a hill allowing a shift by three meters in 20 seconds is not a usual hill. Therefore, the change in height (air pressure) relative to time can be used for the detection.

In a case where the number of walking steps during walking can be detected, the change amount of the value of the air pressure per the predetermined number of walking steps, for example, ten walking steps may be set as the threshold. In regard to stairs, a difference in level of one stairstep is approximately 30 centimeters or the like in average stairs and even in lower stairs, the difference is equal to or higher than 15 centimeters. For example, distinguishing between stairs and a hill may be based on whether a shift by 1.5 meters is observed in ten walking steps. The predetermined number of walking steps can be adjusted depending on the sensitivity of the sensor or required detection accuracy.

The smartphone 1 is capable of detecting whether the user is moving on stairs, whereby reflecting this to a movement distance is made possible. Without the detection on stairs, the movement distance is always calculated by multiplying the number of walking steps by a walking step size not depending on the case of stairs or the case of a road. In contrast to this, when it is possible to detect that the user is moving on stairs, a correct movement distance can be calculated by not converting, to the movement distance, the number of walking steps while the user is moving on the stairs.

Because whether the user is moving on stairs can be detected, it is possible to restrict email browsing and text entry while the user is walking on stairs. With this, moving on stairs safely is ensured. When it is possible to detect whether the user is moving on stairs, the movement of the user can be stored in more detail. Accordingly, calories consumed through the movement can be precisely calculated. The number of times the user has used stairs (the number of stairsteps) per day is notified to the user as a reference of the quantity of exercise, whereby the health assistance can be given thereto. For example, the target number of stairsteps for one day can be also set.

Then, in the processing illustrated in FIG. 5, a case where there is a change in the air pressure and the user is not walking has been determined as that the user is moving on an escalator or an elevator. It is preferable for the smartphone 1 to further determine whether the user is moving on an elevator or moving on an escalator based on the detection results of the respective sensors that detect the movement.

Another example of the processing carried out at Step S26 will be described with reference to FIG. 8 to FIG. 10. The controller 10 determines whether the user is moving at a timing when there is no change in the air pressure at Step S42.

When it is determined that the user is moving at a timing when there is no change in the air pressure (Yes at Step S42), the controller 10 proceeds to Step S48. When it is determined that the user is not walking at a timing when there is no change in the air pressure (No at Step S42), the controller 10 determines whether a movement direction is switched at Step S44.

When it is determined that the movement direction is switched (Yes at Step S44), the controller 10 proceeds to Step S48. When it is determined that the movement direction is not switched (No at Step S44), the controller 10 determines that the user is moving on an elevator at Step S46. When Step S42 is determined as Yes or Step S44 is determined as Yes, the controller 10 determines that the user is moving on an escalator at Step S48.

A graph illustrated in FIG. 9 depicts an example of the change in the air pressure in a case where the user has moved on an elevator without stopping at respective floors. A graph illustrated in FIG. 10 depicts an example of the change in the air pressure in a case where the user has stopped at respective floors on an elevator. FIG. 10 illustrates two examples, namely, the case of going up to upper floors and the case of going down to lower floors. During the movement on an elevator, as illustrated in FIG. 9, moving without stopping at a plurality of floors indicates a change in the air pressure different from that of an escalator. In contrast to this, as illustrated in FIG. 10, stopping at respective floors indicates a change in the air pressure similar to that of an escalator.

Based on whether the user is walking during a stop and whether a direction is changed, the controller 10 makes the determination between an escalator and an elevator. As a result, even in a case where the determination solely based on the change in the air pressure is difficult, it is possible to determine whether the user is moving on an elevator or moving on an escalator.

When the controller 10 is capable of detecting that the user is moving on an elevator, the application to an automatic restriction function of a mobile phone such as incoming call restriction and telephone voice volume restriction within the elevator is made possible.

The controller 10 may employ an approach for the determination considering a time during which the elevator is stopped. When it is determined that the user is moving on an elevator or an escalator, a time during which the air pressure is not changing may be excluded from an object to be determined so that whether the user is moving on an elevator or moving on an escalator is determined based on a slope of the change in the air pressure while the air pressure is changing. The elevator has a larger change in the air pressure than that of the escalator when the ascent and decent of the elevator are exclusively examined. Accordingly, by comparing only the ascent and decent thereof, it is possible to determine which one the user is moving on.

In above-described embodiments, the determination between the two movement methods has been made based on the detection results. However, embodiments may be configured to determine whether or not the user is moving on stairs. Hereinafter, exemplary processing will be described with reference to FIG. 11. FIG. 11 is a flowchart illustrating exemplary control carried out by the smartphone according to embodiments. The controller 10 determines whether the user is walking at Step S52. When it is determined that the user is not walking (No at Step S52), the controller 10 proceeds to Step S58.

When it is determined that the user is walking (Yes at Step S52), the controller 10 determines whether a change amount of the value of the air pressure during a predetermined period is equal to or larger than a threshold at Step S54. A similar value to that of the threshold 102 in FIG. 7 described above can be used as the threshold at Step S54.

When it is determined that the change amount of the value of the air pressure during the predetermined period is equal to or larger than the threshold (Yes at Step S54), the controller 10 determines that the user is moving on stairs at Step S56. When it is determined that the user is not walking (No at Step S52), and when it is determined that the change amount of the value of the air pressure during the predetermined period is not equal to or larger than the threshold (No at Step S54), the controller 10 identifies the movement method based on the result at Step S58.

As described above, instead of making the determination between a hill and stairs, whether or not the user is moving on stairs may be exclusively determined. When it is possible to detect that the user is moving on stairs, various types of services for the movement on stairs can be provided.

The smartphone 1 may be configured to determine whether or not the user is moving on an elevator or an escalator based on the result of the air pressure sensor. Hereinafter, exemplary processing will be described with reference to FIG. 12. FIG. 12 is a flowchart illustrating exemplary control carried out by the smartphone according to embodiments.

The controller 10 acquires a history of the detection result of the air pressure sensor 19 at Step S62. The controller 10 acquires a value of the air pressure from the detection result of the air pressure sensor 19. When the history of the detection result of the air pressure sensor 19 has been acquired, the controller 10 determines whether a change amount of the value of the air pressure during a predetermined period is equal to or larger than a threshold at Step S64. The threshold at Step S64 is set to a proper value that enables the determination of a more sudden change in the air pressure than the change occurring due to climate variations or the like.

When it is determined that the change amount of the value of the air pressure during the predetermined period is not equal to or larger than the threshold (No at Step S64), the controller 10 terminates the processing. In this case, the controller 10 may identify the movement method using the aforementioned methods.

When it is determined that the change amount of the value of the air pressure during the predetermined period is equal to or larger than the threshold (Yes at Step S64), the controller 10 determines whether duration time of a situation where the change amount of the value of the air pressure is equal to or larger than the threshold is within a threshold time at Step S66. The threshold time is a longer time than the predetermined period and one minute is exemplified. The duration of the change in the air pressure is not limited to a case where a state in which the change amount of the value of the air pressure during the predetermined period is equal to or larger than the threshold continues to occur within the threshold time. Accordingly, as long as the state in which the change amount of the value of the air pressure during the predetermined period is equal to or larger than the threshold occurs intermittently, the change in the air pressure is determined as duration. Although the state of the duration is determined based on a time in some embodiments, a period may be employed for the determination. Specifically, the state of the duration may be determined in accordance with a counter based on a clock.

When it is determined that the duration time of the situation where the change amount of the value of the air pressure is equal to or larger than the threshold is within the threshold time (Yes at Step S66), the controller 10 determines that the user is moving on an elevator or an escalator at Step S68. When it is determined that the duration time of the situation where the change amount of the value of the air pressure is equal to or larger than the threshold is not within the threshold time (No at Step S66), that is, it is determined that the duration time is longer than the threshold time, the controller 10 determines that the user is moving on a car or a train at Step S69. Various types of vehicles having a drive source such as a passenger car, a bus, and a truck are exemplified as the car. A gasoline engine, a diesel engine, and a motor driven by electricity are exemplified as the drive source. Various types of vehicles traveling on rails or tracks such as a monorail, a surface car, an electric train, or Shinkansen are exemplified as the train.

The smartphone 1 determines whether the duration time of the situation where the change amount of the value of the air pressure is equal to or larger than the threshold is within the threshold time through the processing illustrated in FIG. 12. When the duration time of the situation where the change amount of the value of the air pressure is equal to or larger than the threshold is within the threshold time, the smartphone 1 determines that the user is moving on an elevator or an escalator. Consequently, it is possible to properly determine the movement state. In the processing illustrated in FIG. 12, when the duration time of the situation where the change amount of the value of the air pressure is equal to or larger than the threshold is longer than the threshold time, it is determined that the user is moving on a car or a train. As a result, it is also possible to identify the movement on a car or a train based on the change in the air pressure. The smartphone 1 may terminate the processing without identifying the movement method in a case where the duration time of the situation where the change amount of the value of the air pressure is equal to or larger than the threshold is longer than the threshold time. In other words, the smartphone 1 may exclusively determine whether or not the user is moving on an elevator or an escalator based on the detection result of the air pressure sensor.

The smartphone 1 may combine the processing illustrated in FIG. 12 with the aforementioned other processing. For example, the smartphone 1 may carry out the processing in FIG. 8 after determining that the user is moving on an elevator or an escalator. The smartphone 1 may combine the processing in FIG. 12 with the processing in FIG. 5. Specifically, the smartphone 1 may be configured not to determine that, even when it is determined that there is a change in the air pressure, the user is moving on an elevator or an escalator in a case where the duration time of the situation where the change amount of the value of the air pressure is equal to or larger than the threshold is longer than the threshold time.

Some embodiments disclosed in this application can be modified without departing from the spirit and the scope of the invention. Furthermore, some embodiments disclosed in this application and modifications thereof can be combined as necessary. For example, some aforementioned embodiments may be modified as follows.

The respective programs illustrated in FIG. 4 may be divided into a plurality of modules, for example. Alternatively, the respective programs may be coupled with another program.

Some aforementioned embodiments have described the smartphone as an example of the apparatus provided with the touch screen. However, apparatuses according to the accompanying claims are not limited to the smartphones. Apparatuses according to the accompanying claims may be mobile electronic devices other than the smartphones. Examples of the mobile electronic devices include, but are not limited to, a mobile phone, a tablet, a mobile personal computer, a digital camera, a media player, an electronic book reader, a navigator, a pedometer, a physical activity monitor, a wearable device, a head-mounted display, a hearing aid, an earphone, a game console, etc. The wearable devices include a watch type, a glasses type, a shoe type, a hair band type, a key type, a necklace type, a collar type, a ring type, a bracelet type, etc.

In order to fully and clearly disclose the technique according to the accompanying claims, some characteristic embodiments have been described. However, the accompanying claims are not construed to be limited to some aforementioned embodiments and should be configured so as to embody all of the modifications and the alternative configurations that a person skilled in the art of the applicable technical field can create within the scope of the fundamental matters indicated in this specification.

Although the invention has been described with respect to specific embodiments for a complete and clear disclosure, the appended claims are not to be thus limited but are to be construed as embodying all modifications and alternative constructions that may occur to one skilled in the art that fairly fall within the basic teaching herein set forth.

What is claimed is:

1. A mobile device, comprising:
an air pressure sensor configured to measure a value of air pressure;
at least one of a direction sensor, an acceleration sensor and a gyroscope; and
a controller configured to estimate a movement method of a user carrying the mobile device based on whether detection results of (i) the air pressure sensor and (ii) the at least one of the direction sensor, the acceleration sensor and the gyroscope continuously satisfy a condition during a certain time, wherein the controller is configured to
acquire the value of the air pressure detected by the air pressure sensor,
determine, as a change amount of the value of the air pressure, a change in the value of the air pressure per a set period,
perform a comparison of the change amount of the value of the air pressure with a reference value,
estimate that the user is moving on stairs in response to
(i) the comparison indicating that the change amount of the value of the air pressure is equal to or larger than the reference value, and
(ii) the at least one of the direction sensor, the acceleration sensor and the gyroscope detecting that the user is walking,
estimate that the user is moving on an escalator or an elevator in response to
(i) the comparison indicating that the change amount of the value of the air pressure is equal to or larger than the reference value, and
(ii) the at least one of the direction sensor, the acceleration sensor and the gyroscope not detecting that the user is walking, and
when the user is estimated to be moving on an escalator or an elevator, estimate that the user is moving on an escalator in response to
(i) the user being detected to be walking for a predetermined distance while the air pressure is not changing, or
(ii) movement direction switching being detected.

2. The mobile device according to claim 1, wherein
the controller is configured to
estimate that the user is moving on a hill in response to
(i) the comparison indicating that the change amount of the value of the air pressure is smaller than the reference value and
(ii) the at least one of the direction sensor, the acceleration sensor and the gyroscope detecting that the user is walking.

3. The mobile device according to claim 1, wherein
the at least one of the direction sensor, the acceleration sensor and the gyroscope is configured to detect whether the user is on board a conveyance, and
in response to the at least one of the direction sensor, the acceleration sensor and the gyroscope detecting that the user is on board a conveyance, the controller is configured to not estimate whether the user is moving on stairs.

4. The mobile device according to claim 1, wherein
the controller is configured to estimate that the user is moving on an elevator or an escalator in response to
(i) the comparison indicating that the change amount of the value of the air pressure is equal to or larger than the reference value, and
(ii) a time during which the air pressure is changing is detected to be within a threshold time, and
the controller is configured to estimate that the user is moving on a car or a train in response to
(i) the comparison indicating that the change amount of the value of the air pressure is equal to or larger than the reference value, and
(ii) the time during which the air pressure is changing is detected to be longer than the threshold time.

5. The mobile device according to claim 1, wherein
the controller is configured to
when the user is estimated to be moving on an escalator or an elevator, estimate that the user is moving on an elevator in response to
(i) the user not being detected to be walking for a predetermined distance while the air pressure is not changing, and
(ii) movement direction switching not being detected.

6. The mobile device according to claim 5, wherein
the controller is configured to estimate that the user is moving on an elevator or an escalator in response to
(i) the comparison indicating that the change amount of the value of the air pressure is equal to or larger than the reference value, and
(ii) a time during which the air pressure is changing is detected to be within a threshold time, and
the controller is configured to estimate that the user is moving on a car or a train in response to
(i) the comparison indicating that the change amount of the value of the air pressure is equal to or larger than the reference value, and
(ii) the time during which the air pressure is changing is detected to be longer than the threshold time.

7. A movement state detection method configured to control a mobile device including an air pressure sensor that measures a value of air pressure and at least one of a direction sensor, an acceleration sensor and a gyroscope, comprising:
estimating a movement method of a user carrying the mobile device based on whether detection results of (i) the air pressure sensor and (ii) the at least one of the direction sensor, the acceleration sensor and the gyroscope continuously satisfy a condition during a certain time, wherein the estimating includes:
acquiring the value of the air pressure detected by the air pressure sensor,
determining, as a change amount of the value of the air pressure, a change in the value of the air pressure per a set period,
performing a comparison of the change amount of the value of the air pressure with a reference value,
estimating that the user is moving on stairs in response to
(i) the comparison indicating that the change amount of the value of the air pressure is equal to or larger than the reference value, and (ii) the at least one of the direction sensor, the acceleration sensor and the gyroscope detecting that the user is walking, estimating that the user is moving on an escalator or an elevator in response to
  (i) the comparison indicating that the change amount of the value of the air pressure is equal to or larger than the reference value, and
  (ii) the at least one of the direction sensor, the acceleration sensor and the gyroscope not detecting that the user is walking, and when the user is estimated to be moving on an escalator or an elevator, estimating that the user is moving on an escalator in response to
  (i) the user being detected to be walking for a predetermined distance while the air pressure is not changing, or
  (ii) movement direction switching being detected.

8. A non-transitory storage medium that stores a movement state detection program for causing a mobile device including an air pressure sensor configured to measure a value of air pressure and at least one of a direction sensor, an acceleration sensor and a gyroscope to execute:

estimating a movement method of a user carrying the mobile device based on whether detection results of (i) the air pressure sensor and (ii) the at least one of the direction sensor, the acceleration sensor and the gyroscope continuously satisfy a condition during a certain time, wherein the estimating includes:

acquiring the value of the air pressure detected by the air pressure sensor, determining, as a change amount of the value of the air pressure, a change in the value of the air pressure per a set period, performing a comparison of the change amount of the value of the air pressure with a reference value, estimating that the user is moving on stairs in response to
  (i) the comparison indicating that the change amount of the value of the air pressure is equal to or larger than the reference value, and
  (ii) the at least one of the direction sensor, the acceleration sensor and the gyroscope detecting that the user is walking, estimating that the user is moving on an escalator or an elevator in response to
  (i) the comparison indicating that the change amount of the value of the air pressure is equal to or larger than the reference value, and
  (ii) the at least one of the direction sensor, the acceleration sensor and the gyroscope not detecting that the user is walking, and when the user is estimated to be moving on an escalator or an elevator, estimating that the user is moving on an escalator in response to
  (i) the user being detected to be walking for a predetermined distance while the air pressure is not changing, or
  (ii) movement direction switching being detected.

* * * * *